(12) United States Patent
Holakovsky et al.

(10) Patent No.: US 9,381,311 B2
(45) Date of Patent: Jul. 5, 2016

(54) SYSTEM COMPRISING A NEBULIZER AND A PACKAGING

(71) Applicants: Holger Holakovsky, Witten (DE); Melanie Herzbach, Heidesheim (DE); Holger Krenz, Dortmund (DE); Heike Rath, Mainz (DE)

(72) Inventors: Holger Holakovsky, Witten (DE); Melanie Herzbach, Heidesheim (DE); Holger Krenz, Dortmund (DE); Heike Rath, Mainz (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 27 days.

(21) Appl. No.: 14/445,638

(22) Filed: Jul. 29, 2014

(65) Prior Publication Data

US 2014/0331994 A1 Nov. 13, 2014

Related U.S. Application Data

(63) Continuation of application No. 13/476,403, filed on May 21, 2012, now abandoned.

(30) Foreign Application Priority Data

May 23, 2011 (EP) .................................. 11004238

(51) Int. Cl.
*B65D 83/20* (2006.01)
*A61M 11/00* (2006.01)
*B65D 83/22* (2006.01)
*B65D 83/56* (2006.01)
*A61M 15/00* (2006.01)
*B65D 81/00* (2006.01)
(Continued)

(52) U.S. Cl.
CPC ........... *A61M 11/00* (2013.01); *A61M 15/0065* (2013.01); *B05B 11/025* (2013.01); *B65D 81/00* (2013.01); *B65D 83/226* (2013.01); *B65D 83/56* (2013.01); *B65D 85/00* (2013.01); *A61M 2205/276* (2013.01); *A61M 2209/06* (2013.01); *B65D 75/002* (2013.01); *B65D 75/32* (2013.01); *B65D 81/05* (2013.01); *B65D 81/325* (2013.01)

(58) Field of Classification Search
CPC ................... A61M 2205/27; A61M 2205/273; A61M 2205/276; A61M 2209/06; B65D 75/002; B65D 75/32; B65D 81/025; B65D 81/05; B65D 81/325; B65D 81/3255; B65D 83/226; B65D 83/56
See application file for complete search history.

(56) References Cited

U.S. PATENT DOCUMENTS 2,720,969 A 10/1955 Kendall
3,802,604 A 4/1974 Morane et al.
(Continued)

FOREIGN PATENT DOCUMENTS

CN 101247897 A 8/2008
DE 2754100 A1 6/1978
(Continued)

OTHER PUBLICATIONS

International Search Report and Written Opinion for PCT/EP2012/058905 mailed Oct. 19, 2012.

*Primary Examiner* — Anthony Stashick
*Assistant Examiner* — Mollie Llewellyn
(74) *Attorney, Agent, or Firm* — Michael P. Morris; Mary-Ellen M. Devlin

(57) ABSTRACT

A system comprising a nebulizer, in particular inhaler, having a pre-installed container is proposed. The system comprises a packaging preventing fluidic connection or opening of the container in a delivery state of the nebulizer.

29 Claims, 12 Drawing

Figure 1:
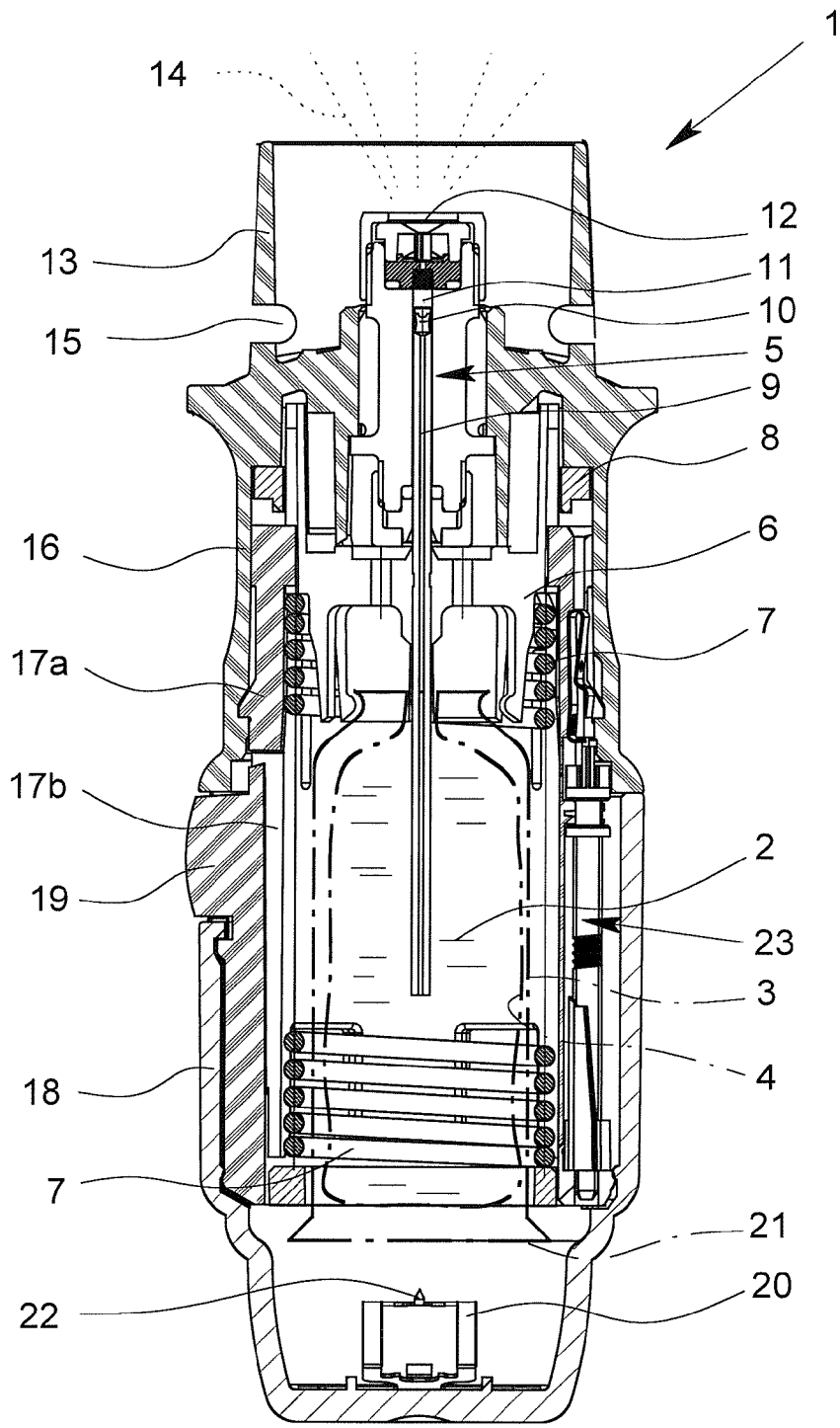

(51) Int. Cl.
    *B65D 85/00*     (2006.01)
    *B05B 11/02*     (2006.01)
    *B65D 75/00*     (2006.01)
    *B65D 75/32*     (2006.01)
    *B65D 81/05*     (2006.01)
    *B65D 81/32*     (2006.01)

(56) References Cited

U.S. PATENT DOCUMENTS

| | | |
|---|---|---|
| 4,749,082 A | 6/1988 | Gardiner et al. |
| 6,120,492 A | 9/2000 | Finch et al. |
| 6,915,901 B2 | 7/2005 | Feinberg et al. |
| 7,823,584 B2 | 11/2010 | Geser et al. |
| 2004/0094147 A1 | 5/2004 | Schyra et al. |
| 2006/0282045 A1 | 12/2006 | Wilkinson et al. |
| 2007/0062518 A1 | 3/2007 | Geser et al. |
| 2007/0107720 A1 | 5/2007 | Boeck et al. |
| 2008/0283553 A1 | 11/2008 | Cox et al. |
| 2009/0032427 A1 | 2/2009 | Cheu et al. |
| 2009/0272664 A1 | 11/2009 | Marshall et al. |
| 2009/0308772 A1 | 12/2009 | Abrams |
| 2010/0237102 A1 | 9/2010 | Margheritis |
| 2011/0005517 A1 | 1/2011 | Boeck et al. |
| 2013/0126389 A1 | 5/2013 | Holakovsky et al. |
| 2014/0331994 A1 | 11/2014 | Holakovsky et al. |

FOREIGN PATENT DOCUMENTS

| | | |
|---|---|---|
| FR | 2673608 A1 | 9/1992 |
| JP | 2008119489 A | 5/2008 |
| JP | 2010526620 A | 8/2010 |
| WO | 2010005946 A2 | 1/2010 |
| WO | 2012159914 A1 | 11/2012 |

SYSTEM COMPRISING A NEBULIZER AND A PACKAGING

The present invention relates to a system comprising a nebulizer, in particular an inhaler, and a packaging and to the use of a packaging for a nebulizer to prevent fluidic connection or opening of a container and/or completely closing of the nebulizer and/or completely inserting of the nebulizer in a delivery state.

WO 2006/125577 A2 discloses a nebulizer which has, as a reservoir for fluid which is to be atomized, an insertable rigid container having an inner bag containing the fluid and a pressure generator with a drive spring for delivering and atomizing the fluid. Preferably, the container is pre-installed in the nebulizer in the delivery state. Before being used for the first time a securing member of the nebulizer, such as a banderole, has to be opened or removed so that a housing of the nebulizer can be completely closed. Thus, the pre-installed container is opened by a delivery tube piercing a sealing and a septum to fluidically connect to the inner bag of the container. By rotating a lower housing part of the housing of the nebulizer the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a releasing element the drive spring is released and the fluid in the pressure chamber is put under pressure by the drive spring and is delivered or atomized through a nozzle into a mouthpiece as an aerosol, without the use of propellant gas.

Object of the present invention is to provide a system comprising a nebulizer and a packaging as well as a use of a packaging for a nebulizer, wherein an optimized or facilitated handling is possible.

The above object is achieved by a system according to claim 1 or by a use according to claim 15. Preferred embodiments are subject of the subclaims.

The container is pre-installed in the nebulizer in the delivery state, in particular at least partly inserted into the nebulizer, but still closed, i.e. not yet fluidically connected to the nebulizer. The packaging is used to prevent fluidic connection or opening of the container in the delivery state and/or to prevent completely closing of the nebulizer, in particular of a housing of the nebulizer, and/or completely inserting of the container into the nebulizer in the delivery state.

The packaging can be detached from the nebulizer or vice versa to allow fluidic connection or opening of the container and/or to allow completely closing of the nebulizer, in particular of the housing of the nebulizer, and/or completely inserting of the container into the nebulizer.

This facilitates handling or use of the nebulizer. In particular, the detachment of the packaging is preferably intuitive or automatic when unpacking the nebulizer or opening the packaging for using the nebulizer. Thus, an intuitive handling can be achieved.

Preferably, the packaging prevents by interlocking or form-fit engagement, i.e. form-fit, completely inserting of the container and/or closing of the nebulizer, in particular of a housing of the nebulizer or of pushing on or in of a housing part of the nebulizer. Thus, undesired opening of the container can be prevented very securely in the delivery state of the nebulizer.

Preferably, the nebulizer comprises a securing means or transportation lock for securing or fixing the container within the nebulizer in the delivery state against axial movement and/or against opening. This securing means or transportation lock is preferably overcome, released or opened during or after opening of the container and/or during or after completely closing the nebulizer, in particular at the end of a closing movement where a housing part is pushed on or in. Thus, the securing means or transportation lock can cooperate with the packaging to (additionally) prevent undesired opening/fluidic connection of the container and/or to prevent undesired overcoming or opening of the securing means or transportation lock in the delivery state.

Preferably, the nebulizer comprises a securing means for holding the pre-installed container such that the container is inseparable from the nebulizer and/or is unmoveably held in the delivery state. In particular, the securing means is ring-like and/or comprises finger-like and/or biased holding elements cooperating with corrugations formed on the container. This allows a very simple realization.

A basic idea of the present invention is that even in its delivery state the nebulizer has a closed container provided— at least partly—therein and the nebulizer is constructed so that the container is opened inside the nebulizer before or during the first use of the nebulizer. This basic idea is called in the present invention also "pre-installed container". This makes operation easier as there is no need to open the nebulizer, insert the container and close the nebulizer. Moreover, undesirable soiling or damage to the nebulizer caused by incorrect handling of the end-user when inserting the container can thus be prevented. Accordingly, there is better operational safety as it is impossible for the container to be wrongly inserted or otherwise misused during insertion.

Preferably, the container is not replaceable and in particular cannot be removed. This again leads to easier operation and hence improved operational reliability. This also prevents the nebulizer from being used or re-used in an undesirable or unauthorized manner.

In particular, the nebulizer cannot be opened and a lower housing part cannot be removed in order to replace the empty container with a full one in an undesirable manner.

The combination of the pre-installed container and the construction which makes the container non-replaceable results in particularly easy operation and high operational reliability as the user can only use the nebulizer as a single-use item until the container is empty, and undesirable or unauthorized further use of the nebulizer is prevented by the fact that the container cannot be replaced.

Figure 2:
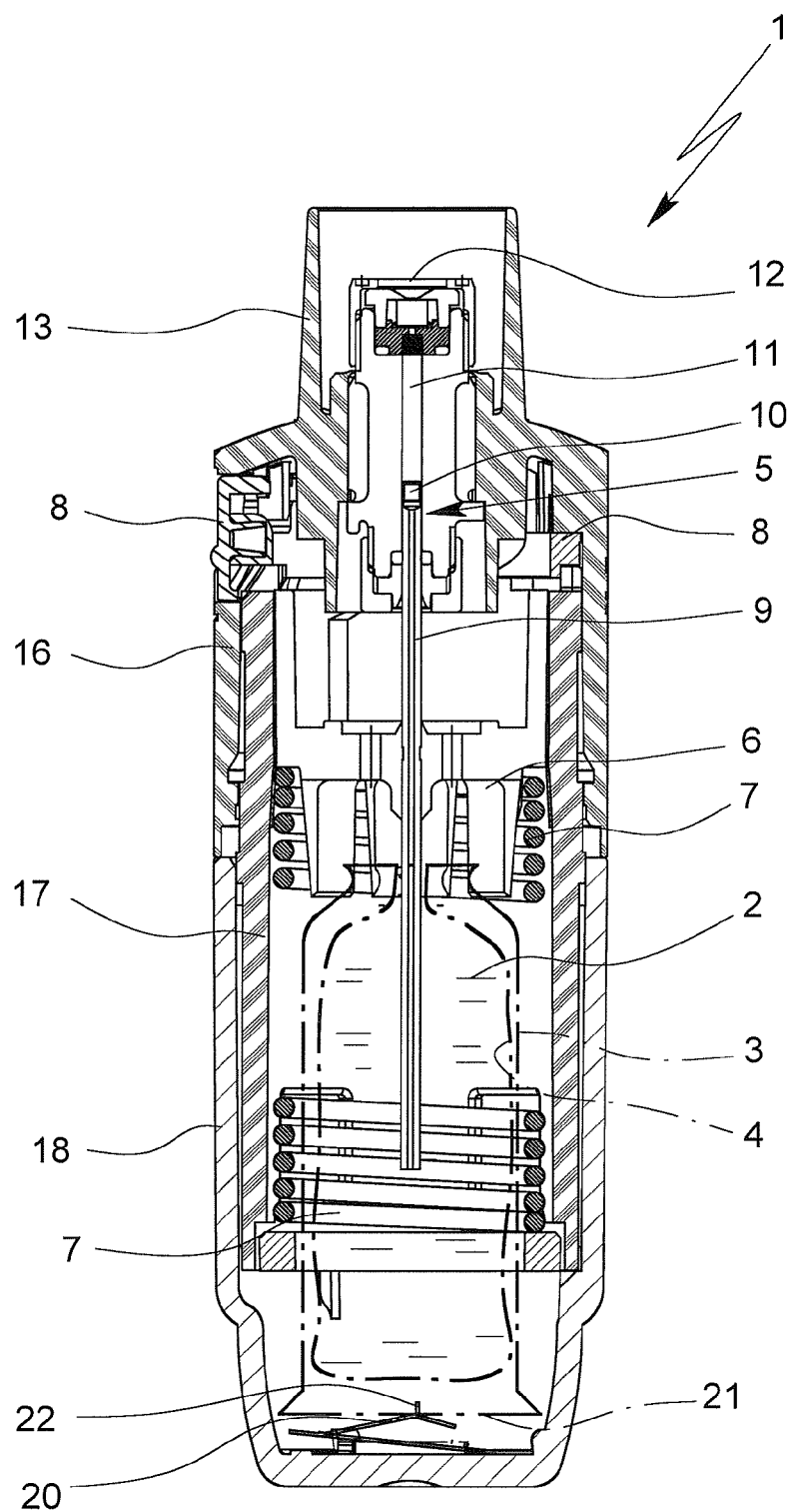
Figure 3:
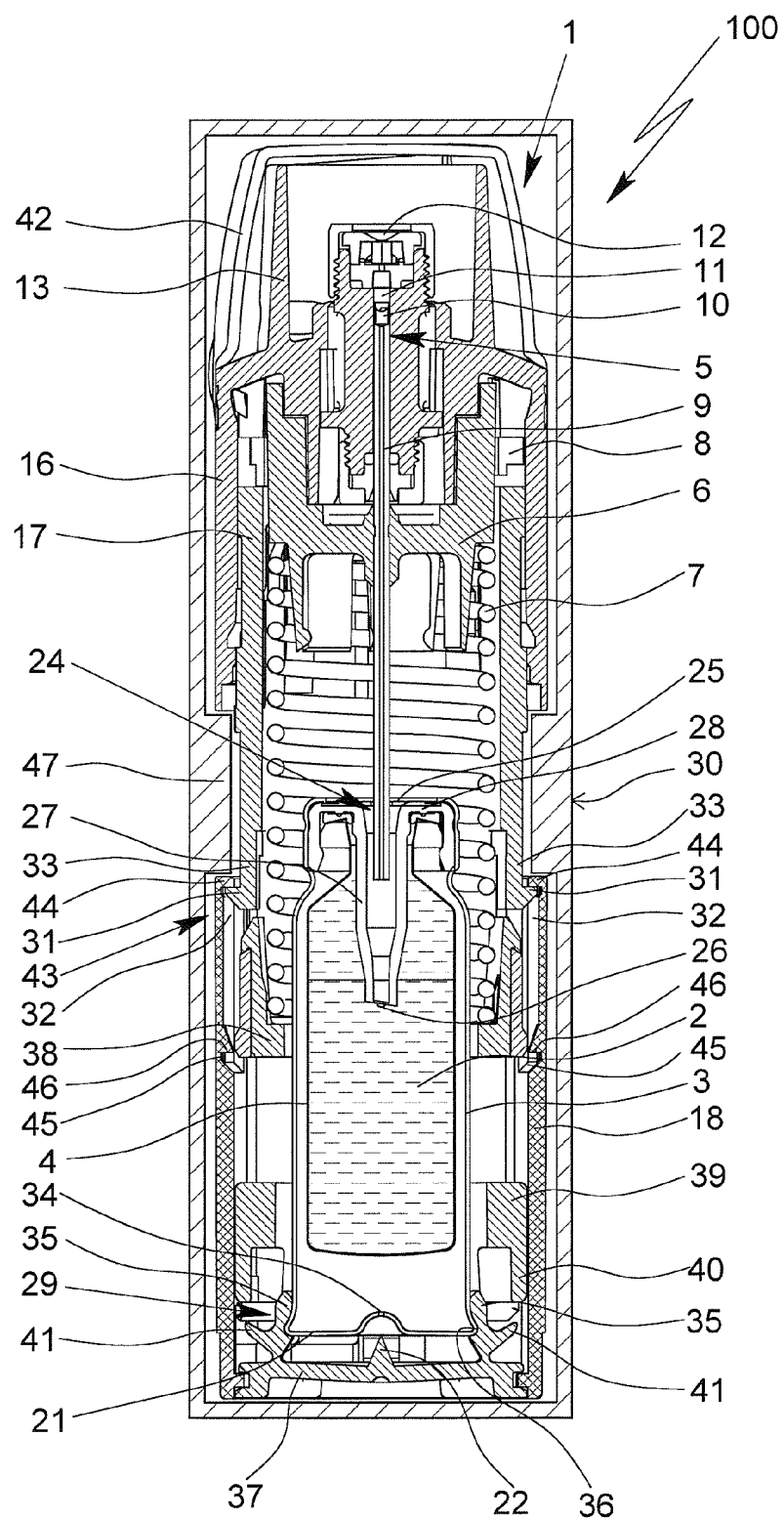
Figure 4:
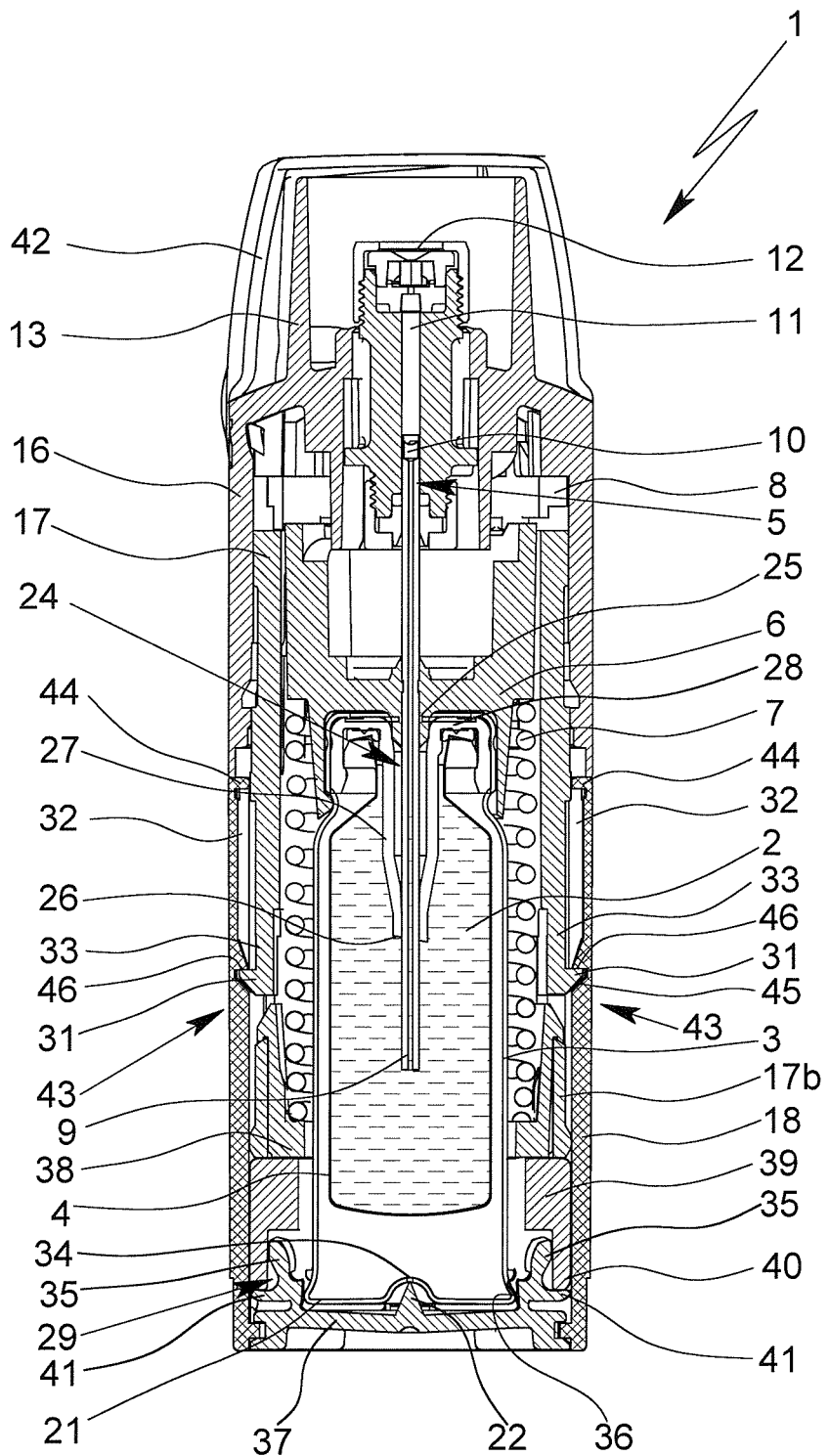
Figure 5:
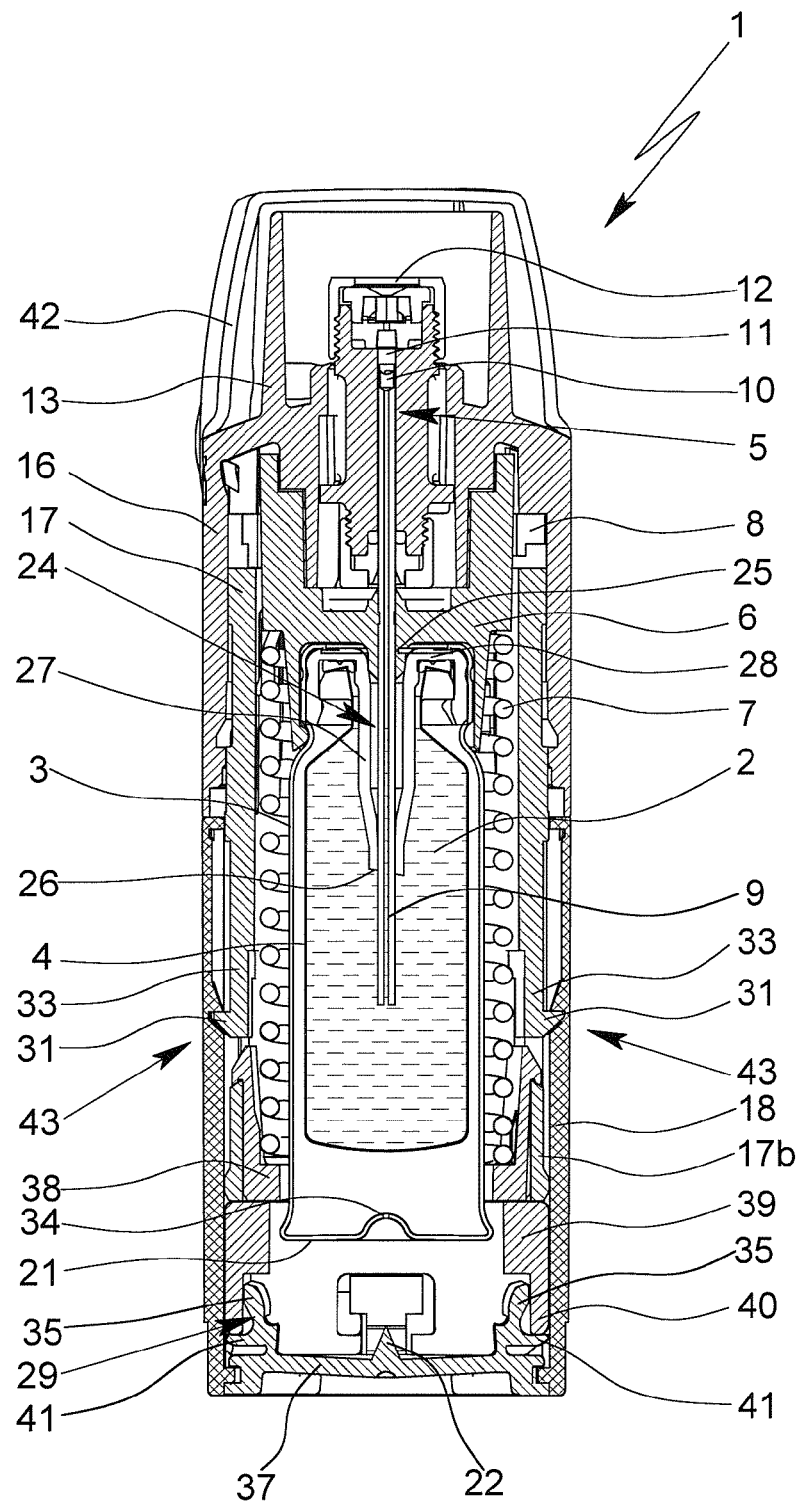
Figure 6:
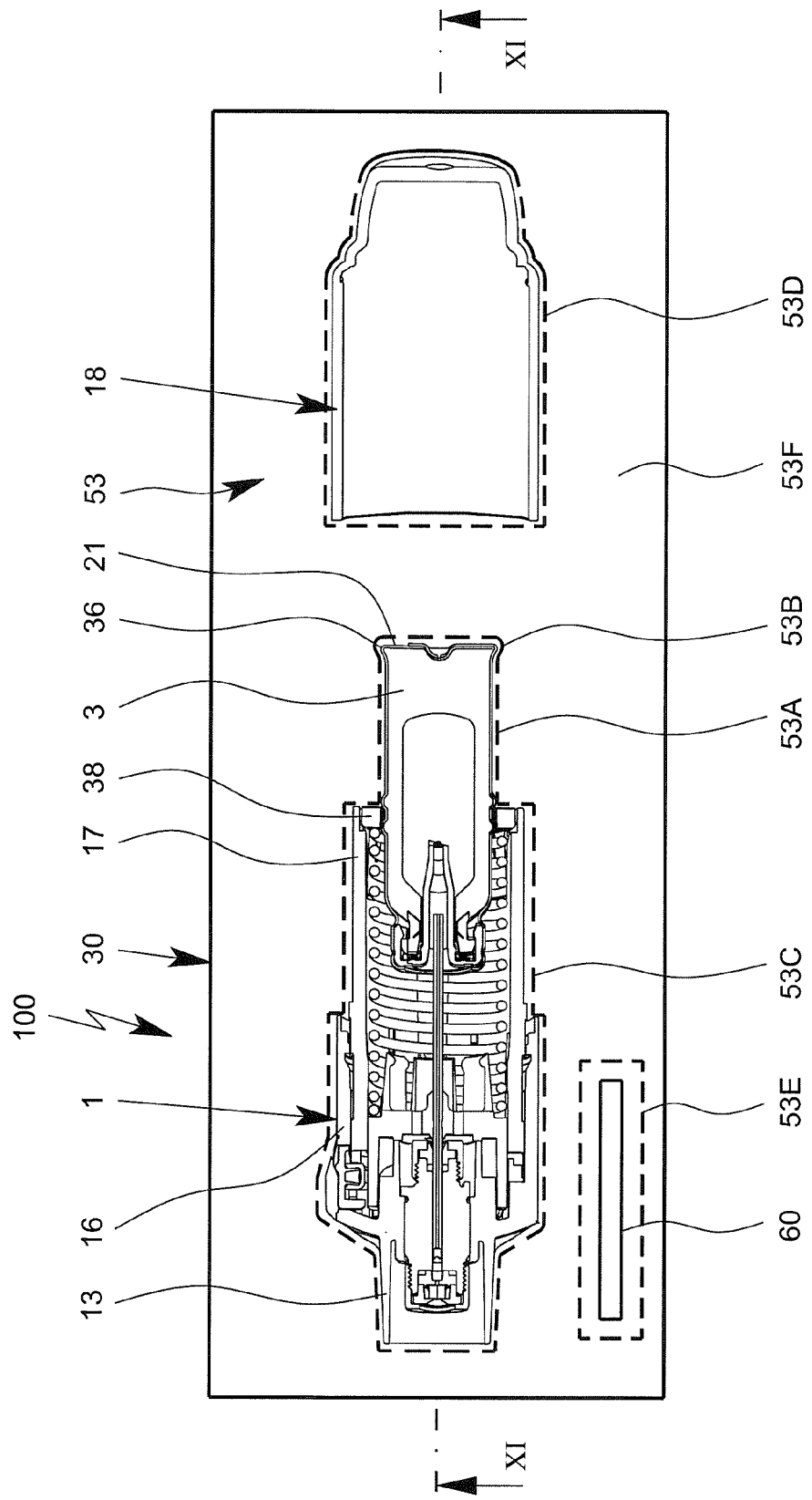
Figure 7:
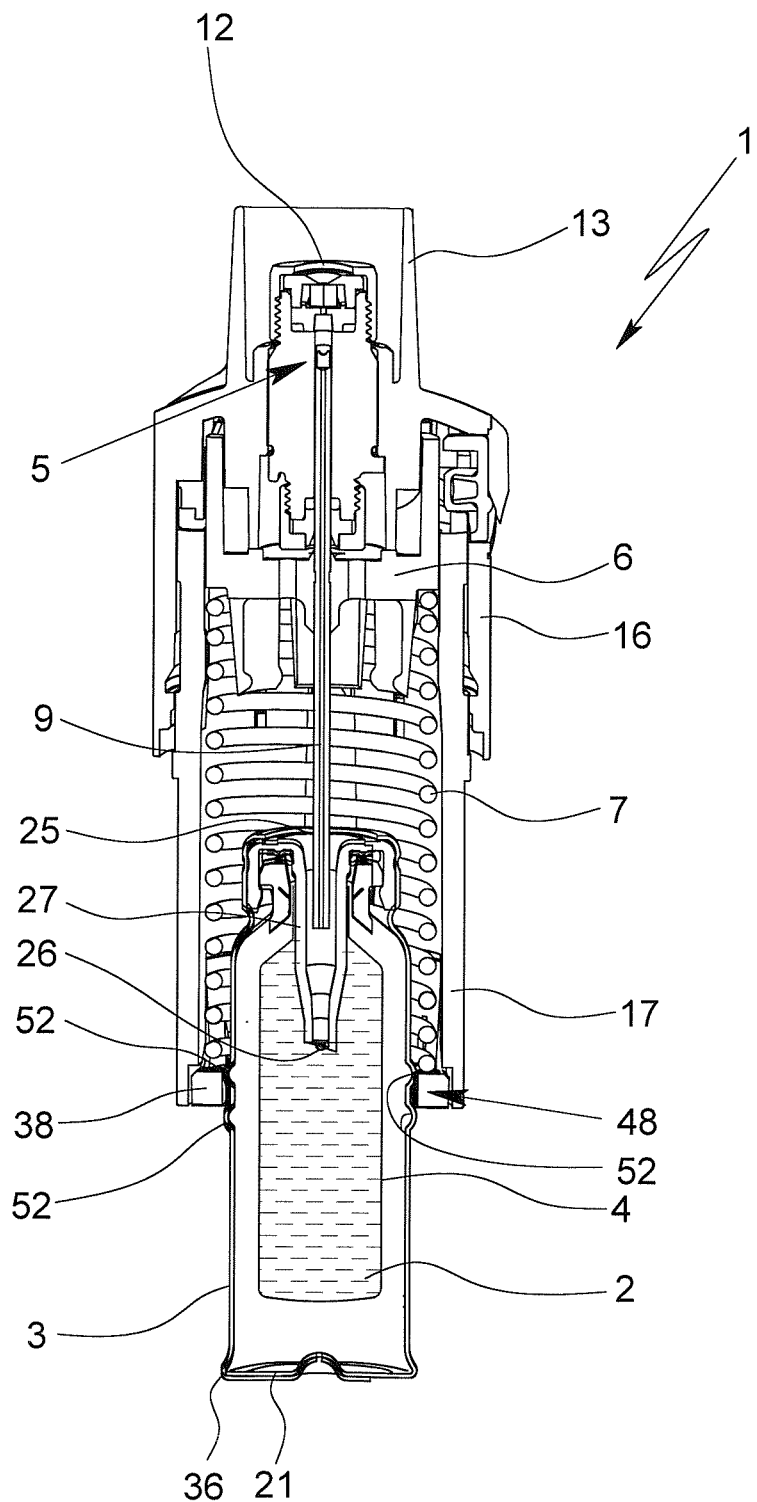
Figure 8:
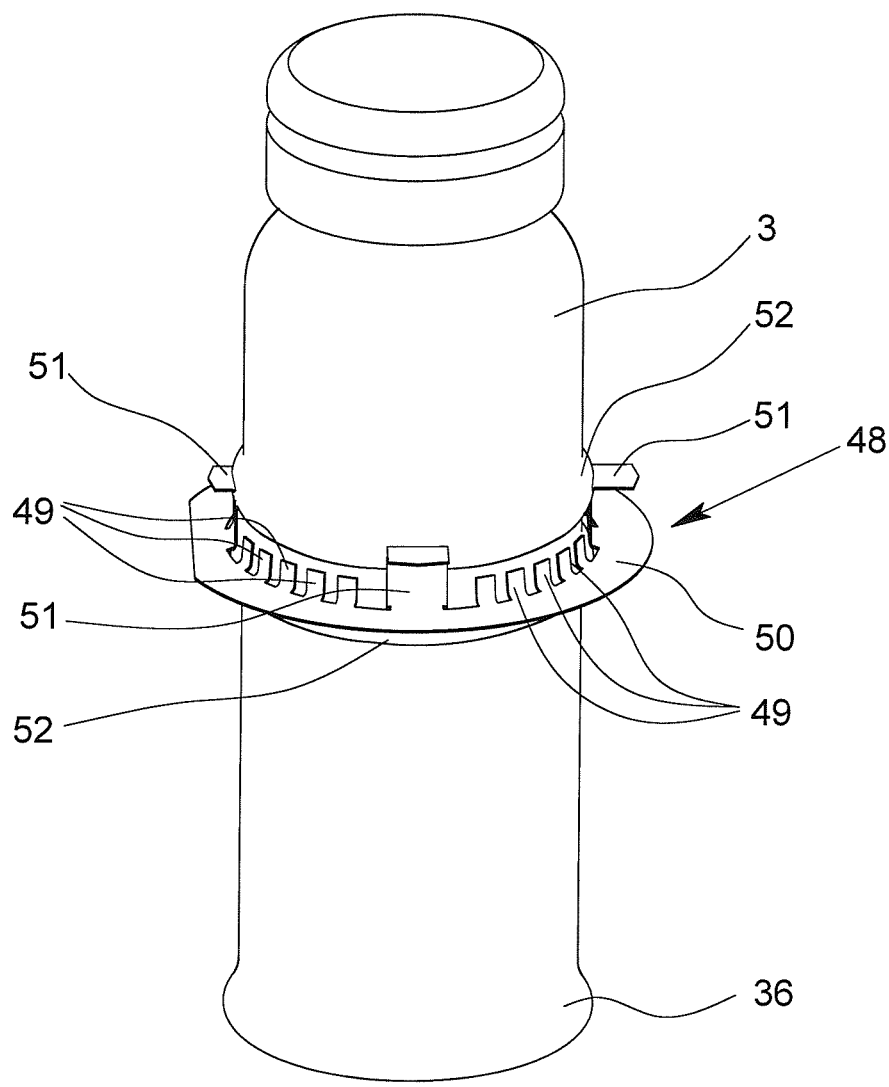
Figure 9:
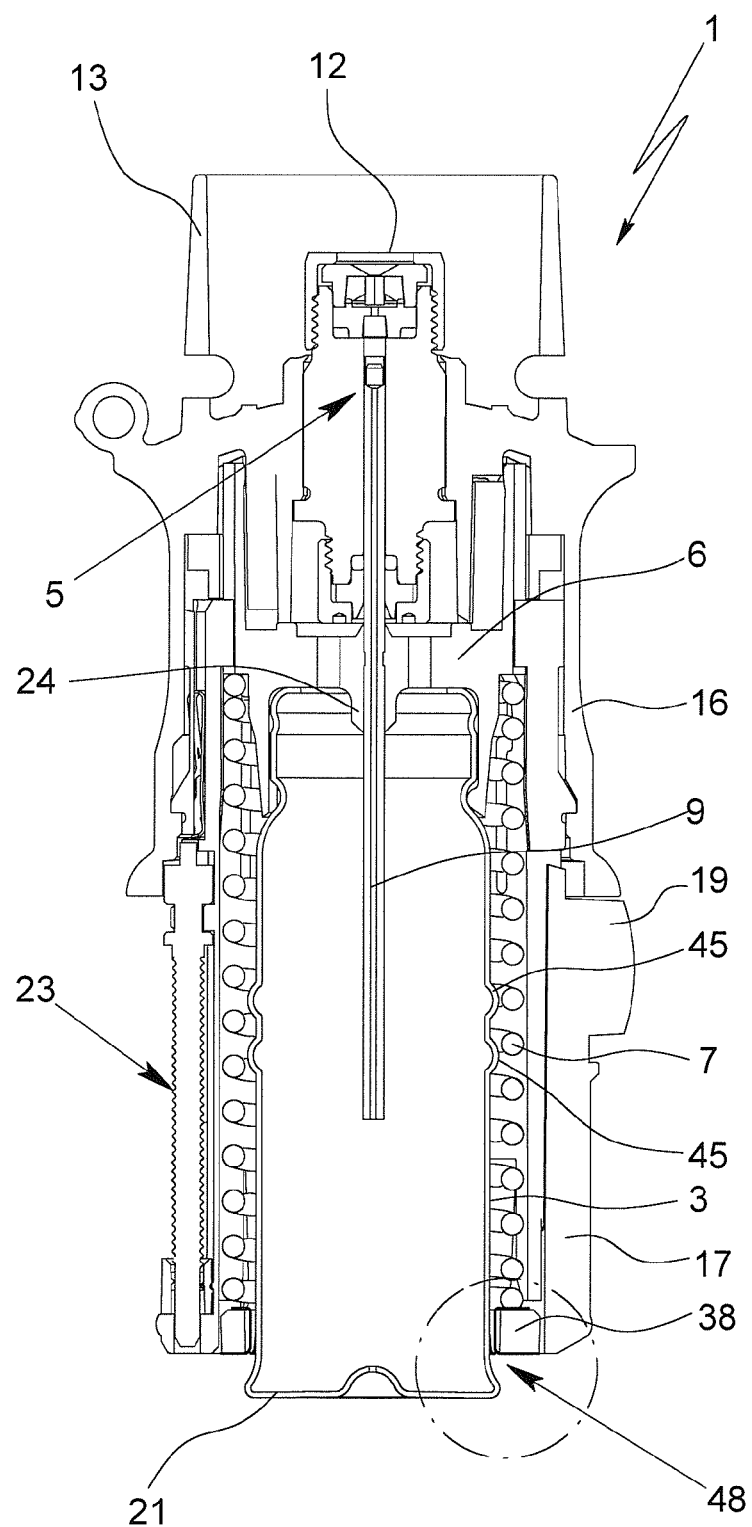
Figure 10:
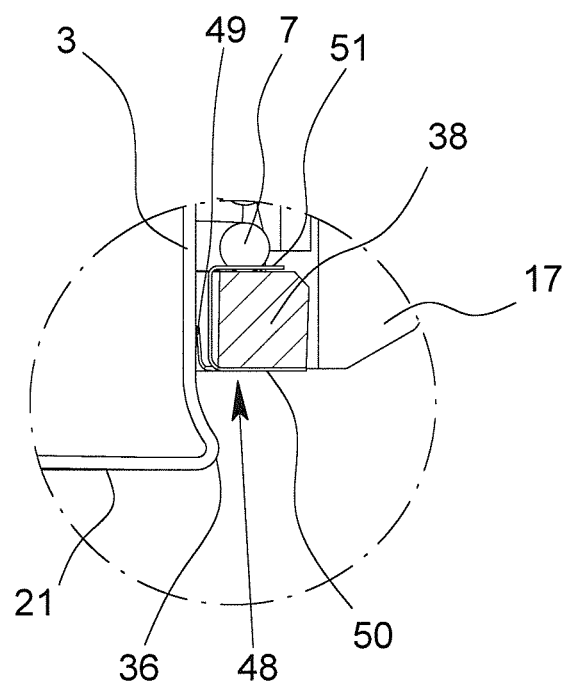
Figure 11:
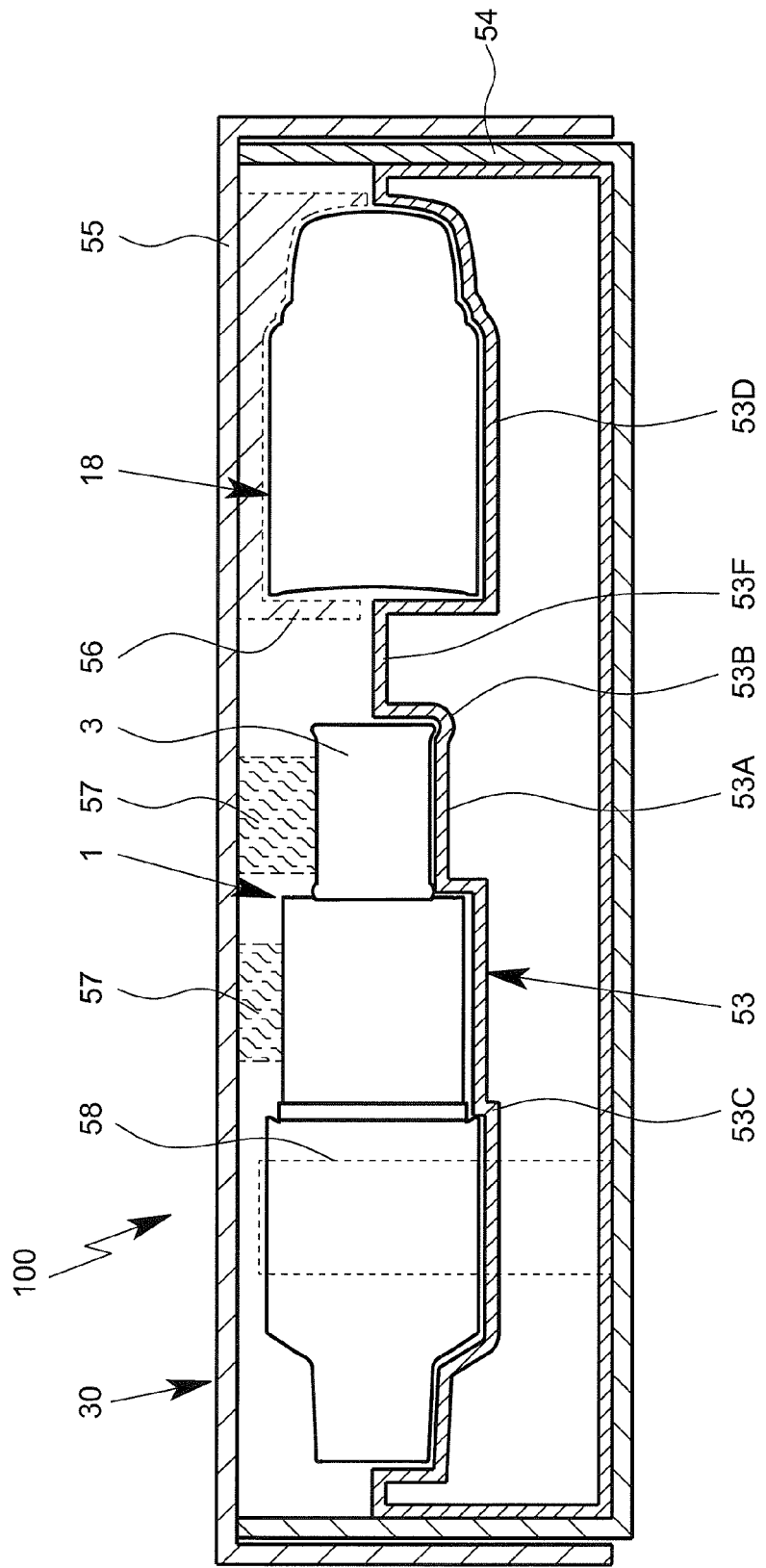

Further advantages, features, characteristics and aspects of the present invention will become apparent from the claims and the following description of a preferred embodiments with reference to the drawings. It shows:

FIG. 1 a schematic section of a known nebulizer in a non-tensioned state;

FIG. 2 a schematic section, rotated through 90° compared with FIG. 1, of the known nebulizer in a tensioned state;

FIG. 3 a schematic section of a system with a nebulizer and a packaging according to a first embodiment of the present invention in a delivery state with a partly closed housing and with a pre-installed, closed container;

FIG. 4 a schematic section of the nebulizer according to FIG. 3 without packaging in an activated or tensioned state with the completely closed housing and with the opened container;

FIG. 5 a schematic section of the nebulizer according to FIG. 4 in a non-tensioned state;

FIG. 6 a schematic view of a system according to a second embodiment of the present invention with a nebulizer according to a modified embodiment and with a packaging according to a second embodiment of the present invention;

FIG. 7 a schematic section of the nebulizer shown in FIG. 6 with pre-installed container held by securing means, but without lower housing part;

FIG. 8 a schematic perspective view of the container and securing means according to FIG. 6;

FIG. 9 a schematic section of the nebulizer shown in FIGS. 6 and 7 with completely inserted container;

FIG. 10 a partial enlarged view of FIG. 9;

FIG. 11 a schematic section of the system along line XI-XI of FIG. 6; and

Figure 12:
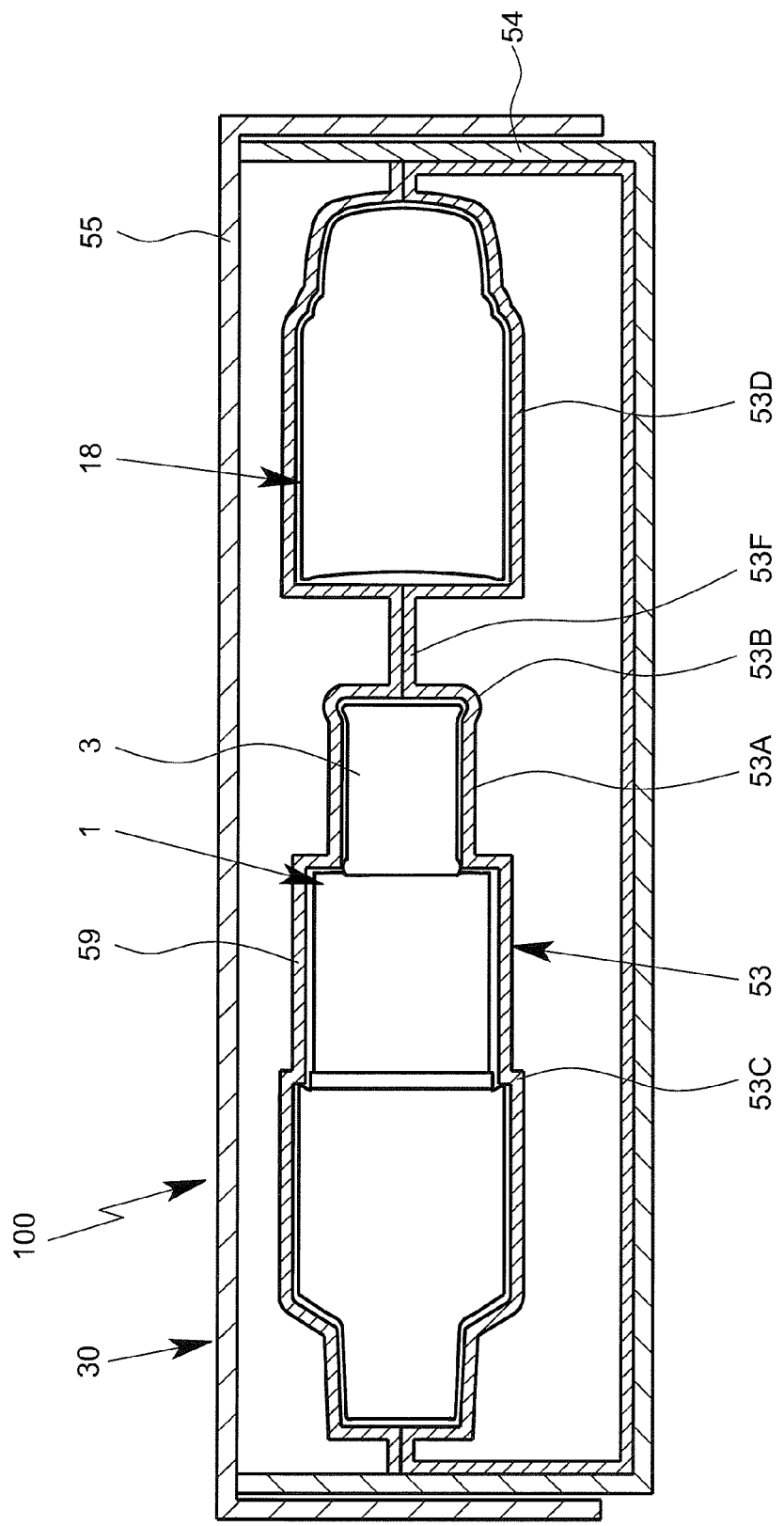

FIG. 12 a schematic section similar to FIG. 11 of the system according to a modified embodiment.

In the Figures, the same reference numerals have been used for identical or similar parts, resulting in corresponding or comparable properties and advantages, even if the associated description is not repeated.

FIGS. 1 and 2 show a known nebulizer 1 for atomizing a fluid 2, particularly a highly effective pharmaceutical composition, medicament or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complain or illness from which the patient is suffering.

The nebulizer 1 is provided with or comprises an insertable or replaceable container 3 containing the fluid 2. The container 3 thus forms a reservoir for the fluid 2 which is to be nebulized. Preferably, the container 3 contains multiple doses of fluid 2 or active substance, in particular sufficient to provide up to 200 dosage units or doses, for example, i.e. to allow up to 200 sprays or applications. A typical container 3, as disclosed in WO 96/06011 A1, holds e.g. a volume of about 2 to 10 ml.

It has to be noted that the dose can vary, in particular depending on the fluid 2 or medicament. The nebulizer 1 can be adapted respectively.

Further, the number of doses contained in the container 3 and/or the total volume of the fluid 2 contained in the container 3 can vary depending on the fluid 2 or respective medicament and/or depending on the container 3 and/or depending on the necessary medication or the like.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally in an adjustable dosage amount. The pressure generator 5 comprises preferably a holder 6 for releasable holding the container 3, a drive spring 7 associated to the holder 3, only partly shown, a locking element 8 which can catch and block the holder 6 and can be manually operated to release the holder 6 allowing drive spring 7 to expand, a conveying element, such as a conveying tube 9, a non-return valve 10, a pressure chamber 11 and/or a nozzle 12 for nebulizing the fluid 2 into a mouthpiece 13. The completely inserted container 3 is fixed or held in the nebulizer 1 via the holder 6 such that the conveying tube 9 penetrates into the container 3. The holder 6 is preferably constructed so that the container 3 can be exchanged.

When the drive spring 7 is axially tensioned in the tensioning process the holder 6 with the container 3 and the conveying tube 9 is moved downwards in the drawings and fluid 2 is sucked out of the container 3 into the pressure chamber 11 of the pressure generator 5 through the non-return valve 10. In this state, the holder 6 is caught by the locking element 8 so that the drive spring 7 is kept compressed. Then, the nebulizer 1 is in the so-called activated or tensioned state.

During the subsequent relaxation in the nebulization process after actuation or pressing of the locking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2 and/or with a volume of fluid 2 delivered per stroke of 10 to 50 µl, preferably 10 to 20 µl, most preferably about 15 µl. The fluid 2 is converted into or nebulized as aerosol 14 the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

Preferably, the nebulizer 1 or drive spring 7 can be manually activated or tensioned, in particular by actuation of an actuation member. The nebulizer 1 comprises preferably an upper housing part 16 and an inner part 17 which is rotatable relative thereto (FIG. 2) having an upper part 17a and a lower part 17b (FIG. 1), while an in particular manually operable (lower) housing part 18 is releasable fixed, particularly fitted or held onto the inner part 17, preferably by means of a retaining element 19. Preferably, the housing parts 16 and 18 form a housing of the nebulizer 1. In order to insert and/or replace the container 3 the housing can be opened and/or the housing part 18 can be detached from the nebulizer 1 or its housing.

The actuation member, preferably the housing part 18, can be actuated, here rotated relative to the upper housing part 16, driving the inner part 17. As a result the drive spring 7 is tensioned in the axial direction by means of a gear or transmission (not shown) formed between the inner part 17, in particular its upper part 17a, and the holding 6 and acting on the holder 6. During tensioning the container 3 is moved axially downwards until the container 3 assumes an end position as shown in FIG. 2. In this activated or tensioned state the drive spring 7 is under tension and can be caught or held by the locking element 8. During the nebulizing process the container 3 is moved back into its original position (non-tensioned position or state shown in FIG. 1) by the drive spring 7. Thus the container 3 executes a lifting or stroke or linear movement or a back and forth movement during the tensioning process or conveying of fluid 2 and/or during the pressure generation or nebulization (process).

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with a base 21 of the container 3 and pierces the container 3 or a base seal thereon with a piercing element 22 when the container 3 makes contact with it for the first time, to allow air in or aeration.

The nebulizer 1 may comprise a monitoring device 23 which counts the actuations of the nebulizer 1, preferably by detecting the rotation of the inner part 17 relative to the upper part 16 of the housing. Preferably, the monitoring device 23 blocks the (further) actuation or use of the nebulizer 1, e.g. blocks the actuation of the releasing element 8, when a certain number of actuations or discharged doses has been reached or exceeded.

FIGS. 3 to 5 relate to a system 100 according to a first embodiment of the present invention. The system 100 comprises or is formed a combination of a nebulizer 1 and a packaging 30 according to a first embodiment of the present invention. The nebulizer 1 shown in FIGS. 3 to 5 differs from the nebulizer 1 according to FIGS. 1 and 2. However, only essential differences from the nebulizer 1 according to FIGS. 1 and 2 will be emphasized or discussed. The remarks relating to FIGS. 1 and 2 thus apply preferably accordingly or in a similar manner, while any desired combinations of features of the nebulizer 1 according to FIGS. 1 and 2 and the nebulizer 1 described below are possible.

Preferably, the container 3 is pre-installed. This can be realized in particular as shown in WO 2006/125577 A2 or as described in the following. In particular, the nebulizer 1 may be constructed and the container 3 may be pre-installed as described in the following with reference to FIGS. 3 to 5. However, other constructional solutions are also possible as explained later.

FIG. 3 shows the system 100 with nebulizer 1 in the packaging 30 in a delivery state, i.e. with pre-installed container 3 which is still closed. In this state, the housing of the nebulizer 1 is not completely closed, in particular the housing part 18 is not completely pushed on the inner part 17. FIGS. 4 and 5 show the nebulizer 1 in an activated state with the housing completely closed and with the container 3 opened. In FIG. 4, the nebulizer 1 or drive spring 7 is tensioned, i.e. the container 3 is in its lower position. FIG. 5 shows the nebulizer 1 in a non-tensioned state, e.g. after dispensing or nebulizing of one dose of the fluid 2, the container 3 is in its upper position.

The container 3 is already mounted or pre-installed in the nebulizer 1 in the delivery state, as shown in FIG. 3. In this state, the container 3 is still closed, i.e. there is no fluidic connection between the container 3 or its bag 4 on one hand and the nebulizer 1 or its pressure generator 5 or the conveying element on the other hand.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

In the non-installed state of the container 3, i.e. before mounting or pre-installation of the container 3 in the nebulizer 1, the fluid outlet 24 is closed optionally by a first or outerclosure 25 and preferably by a second or inner closure 26. In particular, the first closure 25 covers the second closure 26.

The second or inner closure 26 is preferably formed by a septum, a membrane, a plastic seal or the like and/or is provided inside the container 3.

In the preferred embodiment, the first additional or optional first closure 25 is preferably formed by a seal, a foil, a cap or the like, in particular by a metallic and/or composite foil or the like, which is preferably hot-sealed or attached in any other suitable manner on or to a head end or axial end of the container 3. In the shown embodiment, the first closure 25 is formed preferably by a hot-sealed foil with an aluminum layer.

Preferably, the closures 25 and 26 are designed such that separate opening is possible, in particular such that the first closure 25 can be opened independently from the second closure 26 and/or has to be opened before the second closure 26.

Preferably, the closures 25 and 26 are designed such that successive opening is possible by means of one common element, in particular the conveying element or conveying tube 9 or the like, and/or by piercing.

In the preferred embodiment, the first closure 25 and second closure 26 are arranged one after the other and/or spaced in axial direction or direction of the stroke movement of the container 3 or with respect to the main outlet direction of the fluid 2.

Preferably, the second or inner closure 26 is formed or supported by a closure part 27 extending from the outlet or head end of the container 3 into the container 3 or bag 4. The first or outer closure 25 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the first closure 25 is already opened, but not the second closure 26. This is achieved in particular in that the container 3 is not completely inserted into the nebulizer 1 and/or the housing of the nebulizer 1 is closed only partly, i.e. not completely, in the delivery state, preferably by not completely closing or pushing on the housing part 18 in the shown embodiment. Preferably, the housing part 18 is snapped on or inserted only partly in the delivery state.

Generally, the container 3, fluid outlet 24 or closures 25 or 26 are opened in particular by means of a conveying element, such as the conveying tube 9, or the like and/or by piercing or in any other suitable manner. In particular, the opening is achieved by moving the container 3 relative to the nebulizer 1 or conveying element or tube 9 or the like and/or by movement in longitudinal or axial direction.

According to the shown embodiment, the first closure 25 may be already opened in the delivery state, preferably automatically by the nebulizer 1 or the conveying element or tube 9, in particular during or by pre-installing the container 3, i.e. partly inserting the container 3 into the nebulizer 1 and/or partly closing the housing or housing part 18 of the nebulizer 1. In particular, the first closure 25 is opened during or by or when—preferably only partly—inserting the container 3 and/or during, by or when—preferably partly—closing the housing or housing part 18 of the nebulizer 1. However, the second closure 26, such as a septum, still remains closed in the delivery and/or pre-installed state.

Preferably, the both closures 25 and 26 are designed such that, when the conveying element pierces or opens the closures 25/26 any material may not fall into the fluid 2, but will stay connected to the closure part 27 or the like and/or will be pivoted aside.

In the delivery state, the second closure 26 and, thus the container 3 and the fluid outlet 24 remain closed.

In the shown embodiment, the container 3 is preferably held by a securing means or transportation lock 29 in the housing part 18 in the pre-installed and/or delivery state, in particular such that the container 3 cannot move axially in this state.

In the delivery state, the nebulizer 1 or the housing part 18 is secured by the packaging 30 preferably such that the container 3 and/or housing part 18 are held sufficiently spaced from the nebulizer 1 or upper housing part 16 and/or prevented from being completely inserted or pushed on the conveying element or tube 9, the housing or inner housing part 17 or the like and/or such that (complete) opening of the container 3, namely of the second closure 26, is prevented, and/or complete closing of the nebulizer 1 or its housing is prevented, as shown in FIG. 3.

In the delivery state, the packaging 30 or a portion 47 thereof preferably engages with or between the housing parts 16 and 18, so that the housing part or lower part 18 is axially secured or is kept or held sufficiently away or spaced from the upper housing part 16 to prevent (complete) closing of the housing and/or opening of the container 3 and/or to be able to hold the (still) closed container 3 or second closure 26 away from the conveying tube 9.

Preferably, the packaging 30 or its portion 47 block in a form-fit manner or by interlocking engagement completely closing of the nebulizer 1, i.e. prevent fluidic connection or opening of the container 3 in the delivery state.

Preferably, the packaging 30 or its portion 47 comprises or forms a protrusion or indention engaging between the housing parts 16 and 18 in the delivery state. This protrusion or indention is preferably ring-like.

In particular, the packaging 30 encompasses the nebulizer 1 at least essentially completely in the delivery state. For example, FIG. 3 shows the nebulizer 1 within its associated packaging 30, which is partly opened and/or which is shown in a sectional view.

In particular, the packaging 30 covers the nebulizer 1 on at least one side, preferably a longitudinal side, at least essentially completely in the delivery state. For example, the packaging 30 can comprise two more or less complementary halves for receiving the nebulizer 1 in the packed state, i.e. in the delivery state. However, it is also possible that only one half of the packaging 30 or one part of the packaging 30 forms the securing means which prevents fluidic connection opening of the container 3 and/or completely closing of the nebulizer 1 in the delivery state. The other part or half of the packaging 30 can be formed differently and, thus, does not necessarily have to provide the securing function or to form the securing means in the sense of the present invention.

The packaging 30 can form an inner part of a package for receiving the nebulizer 1. In this case, the package may comprise an outer case, cover, tap or the like as well.

The packaging 30 can be made of any suitable material, in particular of foil, plastics, any composite or the like. Further, the packaging 30 can be made of paper.

Preferably, the packaging 30 comprises or is formed by a moulded or thermoformed plastic part. Further, the packaging 30 can comprise or be formed by a blister or the like. Further, the packaging 30 may comprise or may be formed by a shrink film, foil or the like.

The packaging 30 may be combined with or inserted into any other suitable shell, housing, package, such as a box, or the like.

Preferably, the packaging 30 is detached from the nebulizer 1 to allow fluidic connection or opening of the container 3 and/or to allow completely closing of the nebulizer 1, when the nebulizer 1 is unpacked or removed from the packaging 30. During this unpacking or removal, the packaging 30 may be ruptured or destroyed. Alternatively, the packaging 30 could be designed such that it can be opened without destroying it.

When the nebulizer 1 is separated or removed from the packaging 30 or vice versa, the container 3 can be opened (inside the nebulizer 1) and/or the nebulizer 1 or its housing can be closed completely, in particular by pushing in or on completely the housing part 18. Preferably, the complete closing causes that the container 3 is fluidically connected or opened automatically. Further, closing results preferably in that the securing means or transportation lock 29 is opened automatically.

Preferably, the container 3 and/or housing part 18 are held positively or in a form-fit or interlocking manner in the delivery state. This is achieved in the present embodiment in particular by means of the transportation lock 29 acting between the container 3 and the housing part 18, and the packaging 30 acting between the housing part 18 and the housing of the nebulizer 1 or the upper housing part 16 or the like. However, the packaging 30 could also act directly between the container 3 on one hand and the nebulizer 1, its housing, the upper housing part 16, the inner housing part 17 or the holder 6 on the other hand, in particular as described later with reference to FIGS. 6 to 12.

The pre-installed container 3, i.e. its first closure 25, is still closed in the delivery state, i.e. non-activated state with pre-installed container 3. In this non-activated position, the housing part 18 is preferably secured so that it cannot be lost and, in particular, cannot be released. Then, the housing part or lower part 18 of the nebulizer 1 can no longer be detached from the nebulizer 1 after it has been (partially) axially pushed on for the first time, i.e. the nebulizer 1 cannot be opened any longer, with the result that that the container 3 cannot be changed, i.e. cannot be removed again.

In order to secure the housing part 18 in the delivery state or partly pushed-on state against detachment, it may beheld or latched positively or in an interlocking or form-fit manner. Preferably, the housing part 18 is secured by latching means 43 particularly comprising at least one latching lug 31, protrusion, nose or the like of the nebulizer 1 which engages in an associated latching recess 32 in the housing part 18 or the like and, thereby, secures the housing part 18 against axial removal by interlocking engagement. In the present embodiment, the latching lug 31 may be formed by or at a latching arm 33 which can preferably flex. Thus, a ratchet-like—or vice versa—latching means 43 for securing the housing part 18 to the nebulizer 1 or to its housing or the upper housing part 16 is formed. However, other constructional solutions are also possible.

Once the packing 30 has been removed a user (not shown) can push the housing part 18 fully on in the axial direction and thereby open the container 3, i.e. the second closure 26, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9). In this pushed on or activated state, the housing part 18 is preferably secured or axially fixed again by interlocking engagement, i.e. form-fit manner in axial direction, particularly by further engagement of the latching means 43 or by means of some other mechanical securing device.

FIG. 4 also shows the nebulizer 1 or container 3 in the activated state, the container 3, i.e. second closure 26, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a vent opening 34 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

In the delivery state shown in FIG. 3, i.e. with the container 3, namely the second closure 26, (still) closed, the nebulizer 1 can be shipped or delivered to the user. Then, the user can store the nebulizer 1 with the pre-installed container 3. The container 3 will be opened later before or during the first use of the nebulizer 1, namely when removing the packaging 30 and completely closing the nebulizer 1 or housing or housing part 18.

It should be noted that the opening of the container 3 is preferably carried out exclusively by mechanical means and/or manual actuation. However, it is additionally or alternatively possible to open it in other ways, e.g. by chemical, electrical, magnetic, pneumatic, hydraulic or similar means.

The proposed nebulizer 1 is activated after the removal of the 30 and (total) axial pushing on of the housing part 18 and can be used in the same way as the nebulizer 1 shown in FIGS. 1 and 2. The pre-installation of the container 3 prevents the wrong container 3 or used containers 3 from being inserted in the nebulizer 1 by the user. Additionally it ensures that a separately supplied container 3 is not accidentally opened before being inserted in the nebulizer 1. Additionally the proposed solution prevents possible soiling or damage to the nebulizer 1, e.g. the conveying tube 9 or the like, when the nebulizer 1 is opened and the container 3 is used improperly.

As preferably the container 3 cannot then be removed, especially because the nebulizer 1 cannot be opened and the housing part 18 cannot be removed again, undesirable replacement of the container 3 by the user and in particular undesirable interim or subsequent opening of the nebulizer 1 by the user can be prevented.

To prevent unwanted opening of the container 3, particularly of the second closure 26, in the delivery state of the nebulizer 1, preferably the transportation lock 29 is provided. By frictional, forcible or interlocking engagement, for example, the transportation lock 29 prevents the container 3 from undesirably moving axially in the nebulizer 1, e.g. during transportation, in the event of accidental dropping of the nebulizer 1 or the like. Further, the transportation lock 29 may support or hold the container 3 during activation for its fluidic connection or its complete insertion and/or for (completely) connecting the container 3 to the holder 6.

In the following, a preferred realization of the transportation lock 29 will be explained. It has to be noted that the transportation lock 29 can be realized independently from the preferred partial opening or piercing of the container 3 in the delivery state, in particular namely opening of the first closure 25. In particular, the proposed function and construction of the transportation lock 29 can be realized independently from the features of the present claims.

In the preferred embodiment, the transportation lock 29 comprises at least one gripping arm 35, preferably a plurality of gripping arms 35, for axially holding the container 3 in the delivery state, in particular by (radially) engaging around its preferably radially expanded base 21 or edge 36, as shown in FIG. 3.

The gripping arms 35 are preferably held or formed by or attached to or molded unitary with a member 37 which may form the bottom or base or end face of the housing part 18. Preferably, the member 37 or bottom holds the gripping arms 35 such that the arms 35 can flex or pivot.

Preferably, the piercing element 22 is also formed by or held by the member 37.

It has to be noted that the member 37 and/or the transportation lock 29 may be inserted into the housing part 18. The transportation lock 29 or part thereof can also be formed by or in the housing part 18.

Preferably, the transportation lock 29 is formed by multiple or only two different parts, here the gripping arm(s) 35 and a control member 39 as explained later.

The transportation lock 29, in particular the gripping arms 35, are holding the container 3 in the delivery state (closed transportation lock 29) preferably such that the container base 21 or vent opening 34 are axially spaced from the piercing element 22, as shown in FIG. 3.

To open the transportation lock 29, the gripping arms 35 may be flexed radially outwardly. Preferably, the opening of the transportation lock 29 or the flexing of the gripping arms 35 occurs automatically when closing the nebulizer 1 or its housing completely, i.e. when snapping or pushing on the housing part 18 completely towards the upper housing part 16. During this (axial or telescopic) closing movement, the transportation lock 29 is opened and the container 3 released in axial direction preferably only in a last part of the movement and/or just little before the final completely closed position is reached or just when the final completely closed position is reached.

The closing movement of the nebulizer 1 opens the transportation lock 29 preferably automatically. In particular, the transportation lock 29 is opened by the direct or indirect interaction with or actuation by the housing of the nebulizer 1, the inner part 17 or its lower part 17b, a holding ring 38 bearing the spring 7 or the like. Preferably, the container 3 and/or first closure 25 are opened as well as the transportation lock 29 by means of a common actuation, here the closing movement of the nebulizer 1 or its housing or bottom part 18.

In the preferred embodiment, the transportation lock 29 comprises a control member 39, in particular a ring or the like, for actuating or opening or engaging with or pivoting preferably all gripping arms 35 simultaneously. In particular, the control member 39 or transportation lock 29 may convert a linear or axial movement into a pivot or radial movement of the gripping arms 35.

The control member 39 is shown in an upper position in FIG. 3 when the transportation lock 29 is closed. In this position, the control member 39 may secure the gripping arms 35 in the closed positions, in particular in a form-fit manner, e.g. by radially outwardly abutting portions (not shown) of the control member 39 or the like.

The control member 39 is axially moveable or shiftable in order to open the transportation lock 29. In particular, the control member 39 may be moved downwardly when completely closing the nebulizer 1 or its housing or completely pushing or snapping on the housing part 18. Preferably, the inner part 17 or ring 38 pushes the control member 39 downwardly or relatively to the gripping arms 35 so that the gripping arms 35 are released and, in particular, actively or positively opened or pivoted or flexed to open the transportation lock 29 and/or to release the container 3. In the shown embodiment, the control member 39 interacts with its axial end or an axial color or annular ring portion 40 with actuating portions 41 of the gripping arms 35 such that axially downward movement of the actuating portions 41 results in pivotation of the gripping arms 35 and radially outward flexing of the gripping arms 35. The flex characteristics of the gripping arms 35 depend on the used material, on the connection with member 37 and the like.

The control member 39 preferably opens the transportation lock 29 or gripping arms 35 positively.

FIGS. 4 and 5 show the transportation lock 29 and the gripping arms 35 in the open position, i.e. wherein the container 3 is free to move axially. In particular, control member 39 is shown in its downward end position. In this position, the control member 39 is preferably locked or secured within the bottom part 18, in particular by force-fit or form-fit or by a snap-connection, so that the transportation lock 29 and the gripping arms 35 are held open permanently.

However, other constructional solutions of the transportation lock 29 are possible. In this regard, reference is made in particular to WO 2006/125577 A2 which shows some other constructional solutions, which can be realized as well.

FIGS. 3 to 5 show the nebulizer 1 with a mouthpiece cover 42 covering the mouthpiece 13.

In the shown embodiment, the latching means 43 or housing part 18 comprises a first undercut or shoulder 44 associated to the respective latching recess 32 so that the engaging or abutting latching lug 31 holds the housing part 18 in a non-detachable or inseparable manner in the delivery state as shown in FIG. 3. This forms a first form-fit engagement or holding.

The latching means 43 forms or enables preferably a second form-fit engagement or holding of the housing part 18 in the activated state. This is realized in the shown embodiment in that the latching lugs 31 engage into further latching recesses 45 and/or behind second undercuts or shoulders 46 as shown in FIGS. 4 and 5. The second engagement of the latching means 43 is achieved preferably by completely closing the housing or housing part 18 of the nebulizer 1.

It has to be noted that the latching means 43 can be realized e.g. with only one latching lug 31, protrusion, nose, releasing element or the like if desired. In this case, the above description applies preferably as well or in a similar manner.

FIG. 6 shows a second embodiment of the system 100 according to the present invention. The system 100 comprises a nebulizer 1 according to a modified embodiment and a packaging 30 according to a second embodiment of the present invention.

The nebulizer 1 according to the modified embodiment, which is shown in FIG. 7 in an enlarged schematic section, is constructed very similar as the nebulizer 1 described with reference to FIGS. 1 to 5. In particular, the nebulizer 1 according to the modified embodiment comprises or can receive a pre-installed container 3 in the delivery state similar to the embodiment described with reference to FIGS. 3 to 5. The following explanation focuses on essential differences and on new aspects are, so that all previous explanations, in particular regarding FIGS. 1 to 5, apply for the modified embodiment in particular in addition and/or in a corresponding manner.

The nebulizer 1 according to the modified embodiment comprises a securing means 48 for holding the container 3 such that the container 3 is moveable back and forth for the conveying of the fluid 2, pressure generation and/or nebulization in the activated state, but is inseparable from the nebulizer 1 or its inner part 17 and/or is unmovably held in the delivery state. In particular, the securing means 48 forms a transportation lock 29 in the sense described above.

In contrast to the previous embodiment, the container 3 is pre-installed in the delivery state, in particular mechanically connected to the nebulizer 1, independently from the housing part 18. The housing part 18 is connected later or separately to the nebulizer 1 in particular for activating the nebulizer 1, i.e. completely closing the nebulizer 1 and opening the container 3, in particular by pushing the container 3 completely into the nebulizer 1 or its inner part 17. In this respect, it has to be noted that the container 3 may extend with one end or its base 21 out of the nebulizer 1 or inner part 17 even in the completely inserted or activated state as shown schematically in the section according to FIG. 9 (the housing part 18 is still omitted in FIG. 9 for explanation purposes).

Preferably, the securing means 48 comprises or consists of a metal and/or stamping part and/or consists of a single, unitary part as schematically shown in FIG. 8.

Preferably, the securing means 48 is made of steel, in particular spring steel.

Preferably, the securing means 48 is produced from sheet material by cutting, stamping or the like and/or by bending.

Preferably, the securing means 48 is arranged or located at or within the nebulizer 1 or a non-detachable part of the housing or the nebulizer 1, in particular at or in the upper part 16 or inner part 17. In particular, the securing means 48 is located or mounted at or within the ring 38 or any other suitable component and/or preferably at the lower end of the inner part 17. In the shown embodiment, the securing means 48 is arranged at least primarily between the ring 38 and the container 3 as shown in particular in FIG. 10 which is a partial enlarged view of the section according to FIG. 9.

FIG. 8 illustrates in a perspective view the container 3 and the associated securing means 48 in the delivery state. In the shown embodiment, the securing means 48 forms an arrangement of multiple holding elements 49 which are preferably finger-like or leaf-like. In particular, the holding elements 49 are biased and/or inclined towards the container 3.

The holding elements 49 are annularly arranged around a circumference of the container 3 and/or connected with or to a ring portion 50 of the securing means 48. In particular, the holding elements 49 are connected with an inner edge of the preferably flange-like and/or radially extending ring portion 50 and/or extend axially upwards, i.e. in the direction of insertion of the container 3 into the nebulizer 1. The holding elements 49 are inclined radially inwards and/or upwards against the container 3.

The securing means 48 or securing ring formed by the ring portion 50 and the associated holding elements 49 comprises preferably one or more fixing portions 51 for fixing the securing means 48 at the nebulizer 1, its housing or inner part 17, in particular at the ring 38 counter-bearing the drive spring 7. The fixing portions 51 extend preferably in axial direction from the ring portion 50 and are angled radially outwards at its free ends so that a form-fit engagement is possible with ring 38 (ring 38 is axially held between the ring portion 50 and the free ends of the fixing portions 51 extending radially outwards in the preferred embodiment). Thus, the securing means 48 or securing ring can be securely fixed at the ring 38. However, other constructional solutions are possible as well.

The holding elements 49 of the securing means 48 or securing ring cooperate preferably with engagement means formed on or by the container 3 such that the container 3 is moveable back and forth but is inseparable from the housing or nebulizer 1, and/or such that the transportation lock 29 is formed and/or that the container 3 is (axially) unmoveably held in the delivery state.

In the shown embodiment, the container 3 comprises at least one, here two radial shoulders, protrusions or corrugations 52 as engagement means. The corrugations 52 form preferably ring-like ribs or the like on the outer periphery of the container 3 and/or are axially spaced, in particular such that the holding elements 49 can engage inbetween the corrugations 52.

The engagement means or corrugations 52 are preferably arranged or formed on the container 3 such that the holding elements 49 engage—in particular inbetween the two corrugations 52 as schematically shown in FIGS. 7 and 8—in the delivery state such that the container 3 is held axially to avoid complete insertion of the container 3 and/or undesired opening of the container 3 or its second closure 26.

In particular, the upper corrugation 52 prevents that the container 3 can be detached from the nebulizer 1 because the holding elements 49 can not overcome or move over this corrugation 52. Thus, the securing means 48 may prevent replacement of the container 3 at all.

In the opposite direction, the lower corrugation 52 forms an obstacle or resistance for the holding elements 49 so that the container 3 is secured against further insertion in the delivery state, i.e. this corrugation 52 forms together with the securing means 48 or its holdings elements 49 the transportation lock 29. However, this obstacle or resistance can be overcome, i.e. the transportation lock 29 can be opened, by a sufficient high force, e.g. by manually closing the housing (attaching the housing part 18 to the nebulizer 1 or its inner part 17) or manually inserting the container 3, because the holding elements 49 can flex radially outwards so that the lower corrugation 52 can pass and the container 3 can be inserted further, i.e. can move upwards in FIG. 7.

FIG. 9 shows the situation with the fully inserted container 3, i.e. the nebulizer 1 in the activated state (with opened transportation lock 29) with completely opened container 3. The container 3 is connected with holder 6. The drive spring 7 is not tensioned, i.e. FIG. 9 shows the nebulizer 1 in the non-tensioned state. FIG. 10 shows a partial enlargement of FIG. 9 in the area of the securing means 48.

In the activated state, the container 3 can move essentially freely relative to the securing means 48 axially back and forth during the use of the nebulizer 1. However, the holding elements 49 will engage with the engagement means, here first with the lower corrugation 52, when it is tried to separate the container 3 from the nebulizer 1. The two corrugations 52 can provide double security against separation of the container 3 after it has been inserted completely or after the securing means 48 or holding elements 48 have passed lower corrugation 52.

The packaging 30 comprises preferably a base part 53 as schematically shown in FIG. 6.

The base part 53 can form an inner part of a package or of the packaging 30 for receiving the nebulizer 1.

The base part 53 can be made of any suitable material, in particular of foil, plastics, paper, any composite or the like.

Preferably, the packaging 30 or base part 53 is adapted at least partially to the outer contour of the nebulizer 1 in the delivery state and/or is adapted to at least partially receive, hold, support, cover, encompass and/or enclose the nebulizer 1 in the delivery state.

In the second embodiment, the packaging 30 or base part 53 comprises preferably a (protruding or engaging) portion 53A, for engaging with or holding the container 3 and/or engaging between the container 3 and nebulizer 1 or its inner part 17. In particular, the portion 53A engages at or between the lower or free end of the nebulizer 1 or inner part 17 on one hand and a radial or transversal protrusion, shoulder or stop of the container 3, in particular the container base 21 or edge 36 of the container 3, on the other hand.

The portion 53A may contact the container 3 continuously in axial direction from the inner part 17 or ring 38 to the free end or edge 36 of the container 3. Alternatively or additionally, the packaging 30, base part 53 and/or portion 53A may surround or contact the container 3—in particular in its preferably cylindrical portion extending out from the nebulizer 1 or inner part 17 in the delivery state or between the inner part 17/ring 38 and the edge 36 or base 21 of the container 3—in circumferential direction at least partly or completely. In particular, the packaging 30, base part 53 and/or portion 53A may form an at least cylindrical shell or cover or part thereof encompassing the container 3.

Preferably, the packaging 30 and/or base part 53 comprises or forms—in addition or as an alternative to portion 53A—a (holding) portion 53B for (axially) holding or securing the container 3, in particular by form-fit engagement and/or engagement with a shoulder, stop, protrusion, indention, corrugation or the like, here most preferably with the edge 36 (preferably the edge 36 is axially protruding or vided with respect to the essentially cylindrical outer contour of the container 3), and/or a (securing) portion 53C for (axially) holding, securing or counter-bearing the nebulizer 1 or upper part 16, in particular by form-fit engagement or abutment, as schematically shown in FIG. 6.

Thus, the packaging 30, base part 53, portion 53A, portion 53B and/or portion 53C may hold the nebulizer 1 and/or container 3 in the delivery state such that the container 3 is secured against or prevented from fluidic connection or opening of the container 3 and/or completely inserting of the container 3, in particular by form-fit engagement preventing a respective axial movement of the container 3 relative to the nebulizer 1. However, it should be noted that the packaging 30 or base part 53 can hold or secure the nebulizer 1 with the container 3 in the delivery state additionally or alternatively by force fit or friction force against axial movement of the container 3 relative to the nebulizer 1, i.e. against opening of the container 3 or completely inserting of container 3.

Preferably, the packaging 30 or base part 53 is adapted to receive or hold the housing part 18 separated from the nebulizer 1 and/or container 3 in the delivery state according to the second embodiment as shown in FIG. 6. For this purpose, the packaging 30 or base part 53 comprises preferably a (receiving) portion 53D for receiving or holding the housing part 18. However, other constructional solutions are possible.

In the present embodiment, the packaging 30 or base part 53 comprises preferably a (pocket) portion 53E for receiving or holding an optional instruction leaflet 60 of the system 100 or nebulizer 1. The instruction leaflet 60 is preferably intended to explain the use of the nebulizer 1 or system 100.

In the second embodiment, the packaging 30 or base part 53 may comprise a (flat) portion 53F extending one transversally or radially to the nebulizer 1 and/or container 3 and/or in a longitudinal plane of the nebulizer 1 or container 3 and/or at least essentially in one a plane. The portion 53F may be essentially flat. Preferably, the portion 53F interconnects the other portions 53A-D.

The packaging 30 according to the first embodiment does not have such a flat or radially extending base part 53 or portion 53F, but is essentially cylindrical end/or adapted to the outer contour of the nebulizer 1. This adaptation or substantially cylindrical form can be realized also in the second embodiment. In this case, the flat or plane-like portion 53F would be omitted.

FIG. 6 shows the system 100 and packaging 30 according to the second embodiment in a top view without any outer cover. However, the system 100 or packaging 30 may be provided with or comprise additional parts or components, such as an outer package, cover or box, in particular as explained in the following with reference to FIGS. 11 and 12.

FIG. 11 shows in a schematic sectional view a longitudinal section along line XI-XI or FIG. 6 of the system 100 and packaging 30 with the nebulizer 1 in the delivery state and/or in the packed state. FIG. 11. shows additional aspects or features of the system 100 or packaging 30 that can be realized optionally.

In the shown embodiment, the system 100 or packaging 30 comprises preferably an outer shell, housing or box for receiving the base part 53 together with the nebulizer 1 with pre-installed container 3 and (optionally) housing part 18.

Preferably, the system 100 and/or packaging 30 comprises a lower part 54 and/or a cover or upper part 55. Preferably, the lower part 54 and the upper part 55 form an outer box.

The outer box, lower part 54 and/or upper part 55 may be made of paper and/or any other suitable material.

Preferably, the lower part 54 receives the base part 53. In particular, the base part 53 forms an insert or tray holding the nebulizer 1 and, optionally, the housing part 18. The base part 53 is preferably inserted or received in the lower part 54.

The lower part 54 is preferably box-like with a preferably open upper side. The upper side is formed and/or closed in the shown embodiment preferably by the upper part 55. However, the upper side or cover of the lower part 54 can be formed also by a flap, by a pivotable cover or tap or the like. Thus, the outer box or lower part 54 and upper part 55 can be formed by a unitary component or part if desired.

As shown by FIGS. 6 and 11, the packaging 30 or base part 53 may form essentially a half shell, here lower shell, for receiving or holding the nebulizer 1 with the pre-installed container 3 and/or the (separated or spaced) housing part 18.

The system 100 or packaging 30 may comprise or form a complementary contour part 56 and/or a preferably soft and/or elastic holding part(s) 57 for securing and/or holding the nebulizer 1, container 3 and/or housing part 18 at or in the base part 53 or respective receiving areas formed by portions 53A-D.

Alternatively or additionally, the nebulizer 1, container 3 and/or housing part 18 may be secured or held at, on or in the base part 53 or packaging 30 by means of a label, (adhesive) tape, blister or shrink foil 58 or the like as schematically indicated in FIG. 11.

FIG. 12 shows an alternative or modified embodiment of the system 100 or packaging 30 in a schematic section similar to FIG. 11. The packaging 30 comprises an upper or complementary part or cover 59 for securing or holding the nebulizer 1, container 3 and optionally the housing part 18 at or on the base part 53. In particular, the cover 59 is formed by plastic, foil or any other suitable material. In particular, the cover 59 and the base part 53 form together a blister. Preferably, the cover 54 is connected with the base part 53 or flat portion 53 at least partially, preferably by clipsing, welding, gluing or the like.

It has to be noted that the packaging 30 may encompass the nebulizer 1 in the delivery state only partially or at least essentially completely.

The packaging 30 or base part 53 may cover the nebulizer 1 on at least one side, preferably the longitudinal side or bottom side, at least essentially completely in the delivery state as shown in particular in FIGS. 11 and 12.

The packaging 30 or base part 53 may comprise or may be formed by a molded or thermoformed plastic part and/or by an indented insert or tray as already described.

The packaging 30 or parts or portions thereof may be transparent so that a user or patient (not shown) can see the nebulizer 1 and/or container 3 and/or parts thereof.

After detaching or removing the nebulizer 1 from the packaging 30 or base part 53 or vice versa, the nebulizer 1 can be activated, in particular by completely inserting the container 3 and/or (completely) closing the housing of the nebulizer 1, in particular by mounting the housing part 18 to the nebulizer 1 or inner part 17. Then, the nebulizer 1 can be used.

It has to be noted that the FIGS. 6 to 12 show the nebulizer 1 without the optional mouthpiece cover 42. However, the nebulizer 1 will be usually or preferably packed with closed mouthpiece cover 42 although not shown.

Preferably, the packaging 30 or any portion or part thereof forms a seal of originality.

It has to be noted that features of the embodiments and the embodiments described above can be realized independently from each other and combined as desired.

LIST OF REFERENCE NUMERALS

1 nebulizer
2 fluid
3 container
4 bag
5 pressure generator
6 holder
7 drive spring
8 locking element
9 conveying tube
10 non-return valve
11 pressure chamber
12 nozzle
13 mouthpiece
14 aerosol
15 air supply opening
16 upper housing part
17 inner part
17*a* upper part of the inner part
17*b* lower part of the inner part
18 housing part (lower part)
19 retaining element
20 spring
21 container base
22 piercing element
23 monitoring device
24 fluid outlet
25 first closure
26 second closure
27 closure part
28 flange
29 transportation lock
30 securing member
31 latching lug
32 latching recess
33 latching arm
34 vent opening
35 gripping arm
36 edge
37 member
38 ring
39 control member 40 ring portion
41 actuating portion
42 mouthpiece cover
43 latching means
44 first shoulder
45 further latching recess
46 second shoulder
47 portion (packaging)
48 securing means
49 holding element
50 ring portion
51 fixing portion
52 corrugation
53 base part
53A (engaging) portion
53B (holding) portion
53C (securing) portion
53D (receiving) portion
53E (pocket) portion
53F (flat) portion
54 lower part
55 upper part
56 contour part
57 holding part
58 foil
59 cover
60 instruction leaflet
100 system

What is claimed is:

1. A system (100) comprising a nebulizer (1) for delivery of a medicament via inhalation in the form of a fluid (2), and a packaging (30) for receiving and holding the nebulizer (1) in a delivery state, wherein the packaging (30) completely covers the nebulizer (1) on at least a longitudinal side thereof, and wherein the nebulizer (1) comprises a container (3) containing the fluid (2), the container (3) being pre-installed by way of being at least partly pre-inserted into the nebulizer (1) in the delivery state, and the container (3) remaining closed in the delivery state, and wherein the nebulizer (1) comprises a securing means (48) to prevent fluidic connection or opening of the container (3) in the delivery state, and wherein the packaging (30) prevents fluidic connection or opening of the container (3) and prevents complete insertion of the container (3) in the delivery state.

2. The system according to claim 1, wherein the packaging (30) is detachable from the nebulizer (1) to allow opening of the container (3) by complete insertion of the container (3) into the nebulizer (1).

3. The system according to claim 1, characterized in that the packaging (30) engages between an upper housing part (16) of the nebulizer (1) and a lower housing part (18) of the nebulizer (1) in the delivery state such that the housing parts (16, 18) cannot be pushed together completely in the delivery state.

4. The system according to claim 1, characterized in that the packaging (30) engages between the nebulizer (1) and a lower or free end of the container (3) and/or encompasses at least partly the container (3) or a container base (21) and/or holds the container (3) by form-fit in the delivery state.

5. The system according to claim 1, characterized in that the packaging (30) is detached from the nebulizer (1) when the nebulizer (1) is unpacked or removed from the packaging (30).

6. The system according to claim 1, characterized in that the packaging (30) comprises or is formed by a shrink foil (58).

7. The system according to claim 1, characterized in that the packaging (30) comprises or is formed by a molded or thermoformed plastic part (53) and/or by an indented insert or tray.

8. The system according to claim 1, characterized in that the packaging (30) comprises or is formed by a blister.

9. The system according to claim 1, characterized in that the packaging (30) holds a housing part (18) of the nebulizer (1) and/or the container (3) separated or spaced from the nebulizer (1) in the delivery state and/or holds an instruction leaflet.

10. The system according to claim 1, wherein the securing means (48) comprises one or more flexible holding portions (49).

11. The system according to claim 1, wherein the securing means (48) comprises holding portions (49) and wherein the container (1) comprises a engagement means formed on or by the container (3), and wherein the holding portions (49) cooperate with the engagement means in the delivery state.

12. The system according to claim 3, wherein the securing means (48) prevents complete closing of the nebulizer (1) in the delivery state.

13. The system according to claim 1 wherein the securing means (48) holds the container (3) inseparable from the nebulizer (1).

14. The system according to claim 1 wherein the securing means (48) holds the container (3) unmovably in the delivery state whereas the container (3) is movable back and forth for the conveying of the fluid (2) in an activated state of the nebulizer (1).

15. The system according to claim 1 wherein the container (3) is mechanically connected to the nebulizer (1).

16. The system according to claim 1 wherein the securing means (48) comprises a metal part.

17. The system according to claim 16 wherein the securing means (48) is made of steel.

18. The system according to claim 17 wherein the securing means (48) is made of spring steel.

19. The system according to claim 17 wherein the securing means (48) is produced from sheet material by at least one of cutting, stamping and bending.

20. The system according to claim 1 wherein the securing means (48) is arranged within the nebulizer (1) or is a non-detachable part of the nebulizer (1).

21. The system according to claim 1 wherein the securing means (48) forms an arrangement of multiple holding portions (49).

22. The system according to claim 21 wherein the multiple holding portions (49) are finger-like or leaf-like.

23. The system according to claim 21 wherein the holding portions (49) are biased and/or inclined towards the container (3).

24. The system according to claim 21 wherein the holding portions (49) are annularly arranged around a circumference of the container (3) and/or connected with or to a radially extending ring portion (50) of the securing means (48).

25. The system according to claim 24 wherein the holding portions (49) are connected with an inner edge of the radially extending ring portion (50) and extend axially into the direction of insertion of the container (3) into the nebulizer (1).

26. The system according to claim 21 wherein the holding portions (49) are inclined radially inwards and/or upwards against the container (3).

27. The system according to claim 11, wherein the engagement means are one or more circumferentially extending corrugations (52).

28. The system according to claim 27, wherein the corrugations (52) form ring-like ribs on the outer periphery of the container (3).

29. The system according to claim 11, wherein the engagement means comprises two corrugations (52) which are axially spaced, such that the holding portions (49) can engage in between the corrugations (52).

* * * * *